(12) United States Patent
Ettema et al.

(10) Patent No.: US 6,281,360 B1
(45) Date of Patent: Aug. 28, 2001

(54) IMIDAZOPYRIDINE DERIVATIVES AND PROCESS FOR MAKING THEM

(75) Inventors: Gerrit Jan Bouke Ettema, Denekamp; Jacobus Maria Lemmens, Mook; Theodorus Hendricus Antonius Peters, Arnhem, all of (NL); Frantisek Picha, Brno (CZ)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 09/512,789

(22) Filed: Feb. 25, 2000

Related U.S. Application Data
(60) Provisional application No. 60/126,494, filed on Mar. 25, 1999.

(51) Int. Cl.[7] .................................................. C07D 471/04
(52) U.S. Cl. .................................................................. 546/121
(58) Field of Search ............................................. 546/121

(56) References Cited

U.S. PATENT DOCUMENTS

| | | | |
|---|---|---|---|
| 4,382,938 | 5/1983 | Kaplan et al. | 546/121 |
| 4,794,185 | 12/1988 | Rossey et al. | 546/121 |

FOREIGN PATENT DOCUMENTS

| | | |
|---|---|---|
| 0 050 563 B1 | 5/1984 | (EP) . |
| 0 251 859 B1 | 11/1990 | (EP) . |

OTHER PUBLICATIONS

George et al., "Zolpidem and Related Compounds: Syntheses, Physical Properties and Structure–Activity Relationships," *Imidazopyridines in Sleep Disorders*, edited by Sauvanet et al., Raven Press 1988, pp. 11–23.

Schmitt et al., Imidazo[1,2–b]pyridazines. XXIII Some 5–Deaza Analogues. Syntheses of Some 2–Arl–6–(chloro, methoxy or unsubstituted) imidazo[1,2–a]pyridanes and Their Affinity for Central and Mitochondrial Benzodiazepine Receptors, *Aust. J. Chem.* 1997, 50, pp. 719–725.

Trapani et al., "Synthesis and Binding Affinity of 2–Phenylimidazo[1,2–a]pyridine Derivatives for both Central and Peripheral Benzodiazepine Receptors. A New Series of High–Affinity and Selective Ligands for the Peripheral Type," *J. Med. Chem.* 1997, 40, pp. 3109–3118.

*Primary Examiner*—Bernard Dentz
(74) *Attorney, Agent, or Firm*—Mark R. Buscher

(57) ABSTRACT

Imidazopyridine compounds of the formula 1 are can be made in high purity, e.g. greater than 95% pure, by a process that use a novel intermediate of formula 5:

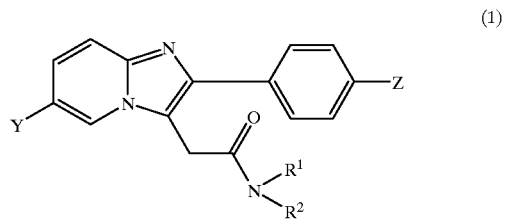

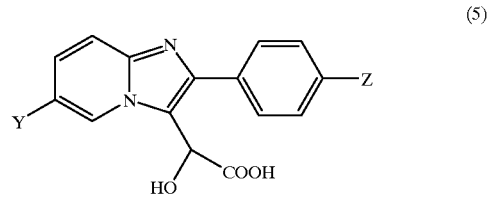

wherein $R^1$ and $R^2$ each independently represent hydrogen or a lower alkyl group and Y and Z each independently represent a lower alkyl group. By this process, zolpidem, a commercial pharmaceutical of the formula 1 can be effectively made.

30 Claims, No Drawings

IMIDAZOPYRIDINE DERIVATIVES AND PROCESS FOR MAKING THEM

This application claims the benefit of priority under 35 U.S.C. 119(e) from prior provisional patent application serial number 60/126,494, filed Mar. 25, 1999, the entire contents of which are hereby incorporated herein by reference.

BACKGROUND OF THE INVENTION

The present invention relates to a synthetic route for producing various imidazopyridine derivatives, to certain intermediates useful therein, and to highly pure compounds produced thereby.

Imidazopyridines of the formula (1) are described in U.S. Pat. No. 4,382,938 as useful pharmaceutical agents.

the commercial product zolpidem which is sold in the hemitartrate form under the brand names Stilnox, Stilnoct, and Ambien. Zolpidem has the following formula.

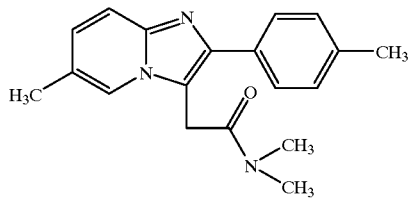

The method disclosed in the above-cited patent for making the compounds of formula (I) can be outlined as follows:

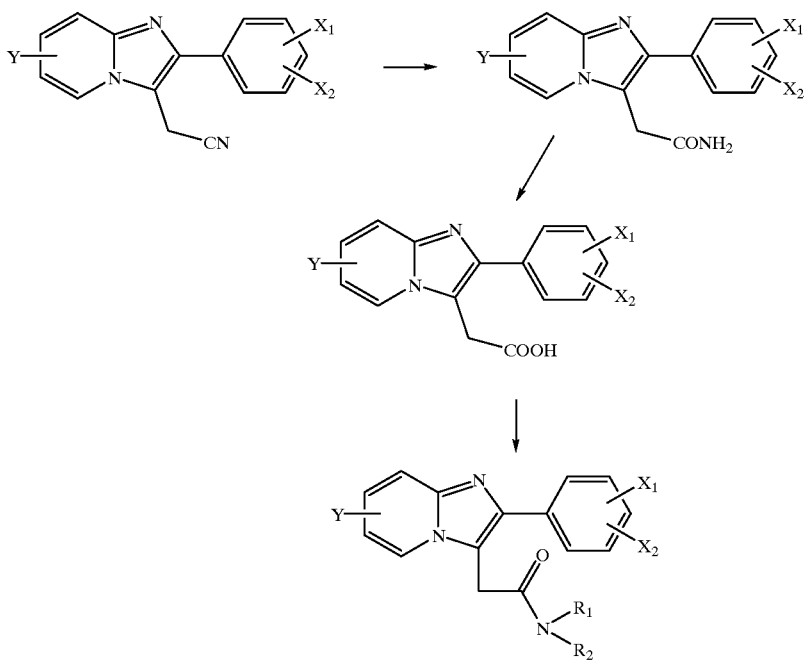

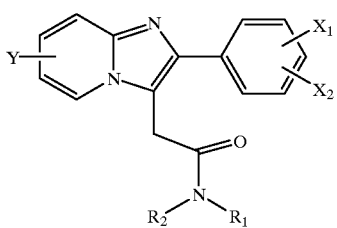

Y is hydrogen, halogen, or $C_1$–$C_4$ alkyl and $X_1$ and $X_2$ are independently a hydrogen, halogen, $C_1$–$C_4$ alkoxy, $C_1$–$C_6$ alkyl, $CF_3$, $CH_2S$, $CH_3SO_2$ or $NO_2$. $R_1$ and $R_2$ are independently hydrogen, $C_1$–$C_5$ alkyl, which may be substituted with, inter alia, halogen, hydroxy, etc., or together they form a heterocyclic ring. The compounds of formula (I) include The nitrile compound is converted to the primary amide compound by conventional methods and then the amide is saponified to form the acid compound. The acid compound can be converted to the final tertiary amide by known techniques including a reaction with an amine of the formula $HNR_1R_2$ in the presence of carbonyldiimidazole or by forming the chloride of the acid and then reacting with amine of the formula $HNR_1R_2$.

This process suffers from several drawbacks, especially from the commercial point of view. For example, the starting nitrile must be formed from the corresponding imidazopyridine compound (unsubstituted in the 3 position) which adds additional synthetic steps. Moreover, the use of toxic reactants such as potassium cyanide are required. A shorter reaction scheme that avoids the use of highly toxic reagents would be advantageous.

An improved synthesis scheme, as shown below, is disclosed in U.S. Pat. No. 4,794,185.

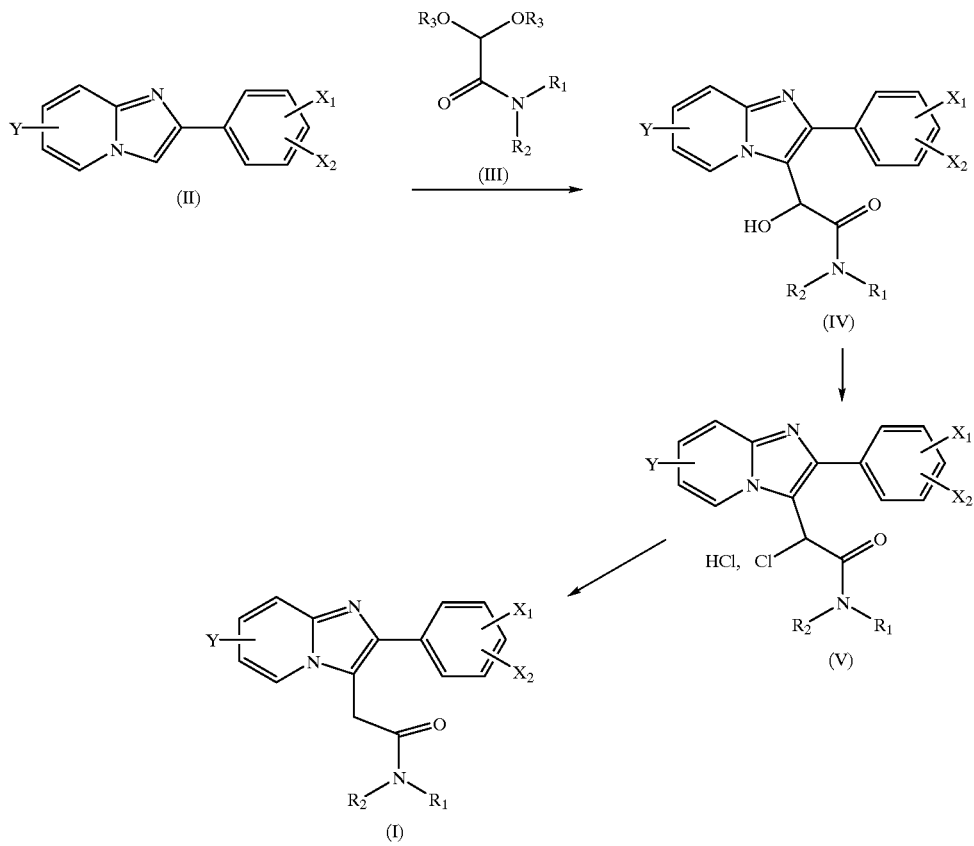

The above process is believed to correspond to the commercial process presently used for the production of zolpidem. The process is described in the patent as providing high yield with "excellent purity, after work up." While the number of steps has been reduced over the earlier process and the use of potassium cyanide can be avoided, the process uses special reactants, specifically the compounds of formula (III). Moreover, the replacement of the hydroxyl group with a chloride to form the compound of formula (V) and its subsequent removal means that chloride is a potentially troubling impurity in the final product. In addition, chlorination agents such as thionylchloride are highly hazardous compounds; making this synthetic scheme potentially dangerous to the operators and the environment. It would be desirable to have a process that could use inexpensive and safe reactants and that could form the free base of the final compound with very high purity.

Additional methods for making various imidazopyridines are disclosed by Schmitt et al., Aust. J. Chem., 1997, 50, 719–725. Among them is the reaction of certain 2-phenylimidazo[1,2-a]pyridines with freshly distilled ethyl glyoxylate to form ethyl 2-hydroxy-2-(2'-phenylimidazo[1,2-a]pyridin-3'-yl) acetate. This compound is reduced by adding phosphorous tetraiodide in dichloromethane to form ethyl 2-(2'-phenylimidazo[1,2-a]pyridin-3'-yl) acetate. Regarding such a procedure, Schmitt et al. states "The foregoing method of preparing the 2-hydroxyacetate and its conversion into the acetate may provide a convenient synthesis of the relevant intermediates for the preparation of alpidem and zolpidem."

Exactly what the alpidem or zolpidem intermediates would be and how they would be used (the intended synthesis scheme) is not explained. Indeed, it is not possible to directly convert the ester compounds of Schmitt et al. to the desired amide using conventional amidation techniques. Moreover, the use of ethyl glyoxylate is not convenient for a commercial scale production. Such a product is commercially sold, apparently exclusively, as a 50% toluene solution. In such a solution, a portion of the ethyl glyoxylate exists in a partly polymerized, and thus unreactive, form. De-polymerization can be carried out by heating. This appears to explain the need to use freshly distilled ethyl glyoxylate as taught in Schmitt et al. Besides the impracticability of using ethyl glyoxylate, the only disclosed reducing agent, phosphorous tetraiodide, is expensive, not readily available, and produces iodine- and phosphorous-containing wastes. Furthermore, Schmitt et al. teaches the isolation of the intermediates by column chromatography. These reactants and procedures are not convenient for scale up to a commercial size production.

Accordingly, it would be desirable to have a process that can use inexpensive and/or readily available reactants. It would also be desirable to have a process that can be readily scaled up, that does not require special purification techniques and that can produce a highly pure product.

SUMMARY OF THE INVENTION

The present invention relates to a process, which comprises reacting a compound of formula (2):

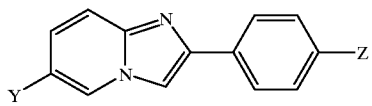

(2)

wherein Y and Z each independently represent a lower alkyl group; with glyoxylic acid or a compound of formula (6):

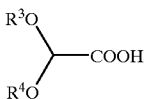

(6)

wherein $R^3$ and $R^4$ each independently represent hydrogen or a lower alkyl;

to form a compound of formula (5).

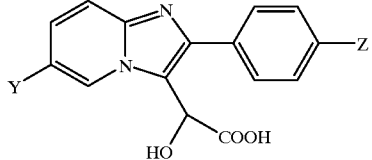

(5)

Further, the present invention relates to removing the alpha hydroxyl group of the compound of formula (5) with a hydrogenolysis agent in the presence of a hydrogenolysis catalyst to thereby form a compound of formula (3).

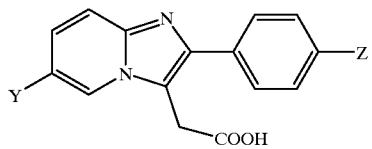

(3)

The compounds of formula (3) can be converted into compounds of formula (1) by the use of an amidation agent;

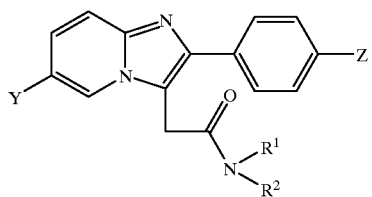

(1)

wherein $R^1$ and $R^2$ each independently represent hydrogen or a lower alkyl group.

The process of the present invention can produce compounds of formula (1) in very high purity, even higher than 99.5%, through the use of common reactants and is susceptible of being scaled. The compounds of formula (5) as well as the highly pure compounds of formula (1) are additional aspects of the invention.

DETAILED DESCRIPTION OF THE INVENTION

The starting compounds of formula (2) are commercially available and/or readily attained by methods known in the art. Y and Z each independently represent a lower alkyl group. As used throughout this specification, the term "lower alkyl group" means a straight chain, branched chain, or cycloalkyl group having 1 to 6 carbon atoms for a straight chain and 3 to 6 carbon atoms for a branched chain or cycloalkyl group. Typically Y and Z represent methyl, ethyl, propyl (n-or iso-propyl), or butyl (n-, iso-, or t-butyl), and preferably are both methyl.

Glyoxylic acid (CHO—COOH) and the compounds of formula (6) are also commercially available or readily attainable by known techniques. The compounds of formula (6) are derivatives of glyoxylic acid. Glyoxylic acid itself is an unstable compound so that it easily forms in a water solution a geminal diol compound (2,2-dihydroxyacetic acid also known as glyoxylic acid monohydrate-formula (6) where $R^3=R^4=H$). This monohydrate form is stable as both a solid crystal and as a water solution. Similarly, glyoxylic acid readily reacts with an alkanol to yield the corresponding acetal (formula (6) where at least one of $R^3$ and $R^4$ is not H). $R^3$ and $R^4$ each independently represent hydrogen or a lower alkyl group. Typically, $R^3$ and $R^4$ are both hydrogen, methyl or ethyl, although they are not limited thereto.

In the "reaction," the compounds of formula (6) are believed to convert to glyoxylic acid as an intermediate which then reacts with the compound of formula (2). In a certain sense, the reaction is thus always between glyoxylic acid and a compound of formula (2). The compounds of formula (6) serve as a convenient precursor compound for providing the active but unstable glyoxylic acid for reaction. It is, however, possible to add glyoxylic acid itself as the reactant to form the compounds of formula (5). The phrase "reacting a compound of formula (2) with glyoxylic acid or a compound of formula (6)" is meant to include all reactions involving glyoxylic acid and the imidazoles of formula (2), whether the glyoxylic acid is directly added or provided indirectly as a precursor, such as the compounds of formula (6). In one embodiment, the glyoxylic acid is provided by adding only a compound or compounds of formula (6).

The condensation reaction of the compound of formula (2) and glyoxylic acid or the compound of formula (6) proceeds smoothly by simple heating of the mixture of both reactants in a suitable inert solvent, optionally with removal of the formed water such as by distillation. Suitable solvents include non-polar organic solvents such as hydrocarbons or chlorinated hydrocarbons having a boiling point of 80° to 150° C. Preferred solvents are those that form an azeotropic mixture with water. Dichloroethane is an example of such a solvent. The glyoxylic acid or compound of formula (6) can be used in either a solid monohydrate or in a water solution and is generally combined in a molar ratio of at least 1:1 but generally not more than 10:1 from the point of view of economy, relative to the amount of 2-phenylimidazo[1,2a] pyridines of formula (2). The addition is carried out on the 3-position exclusively, thereby forming the compound of formula (5).

The produced hydroxyacids of formula (5) are generally solids and can be isolated if desired by techniques well known in the art such as by filtration from a solvent in which it is insoluble or by extraction and evaporation of the extraction solvent. However, in one embodiment such isolation does not occur and the reaction mixture is instead directly used in the next synthetic step. To accomplish this, the solvent should be a suitable medium for both the addition reaction and the subsequent hydroxyl-removal reaction. A preferred example of such a solvent is formic acid.

The substituents Y and Z have the same meaning and preferences as stated above for formula (2). In particular, the compound of formula (5) where Y and Z are both methyl (6-methyl-2-(p-methylphenyl)imidazo[1,2a]pyridine-3-(2'-hydroxy) acetic acid) is a preferred intermediate.

The alpha-hydroxyl group of the compound of formula (5) is subsequently removed and replaced by hydrogen to form an acid compound of formula (3). While many removal techniques and conditions are generally known and principally suitable for use in the present invention, care should be taken to not attack the carbonyl or hydroxyl moieties of the acid group. Only the alpha hydroxyl group is intended to be removed, that is selective removal. To this end, a preferred technique involves hydrogenolysis whereby the hydroxyl group is replaced with hydrogen by the use of a hydrogen source in the presence of a hydrogenolysis catalyst. Hydrogen sources include formic acid, phosphonic acid, phosphinic acid, alkali metal salts of these acids and hydrogen gas, but are not limited thereto. Hydrogenolysis catalysts include palladium, platinum, and rhodium, optionally supported such as on carbon. A preferred combination is formic acid and a palladium or rhodium catalyst supported on carbon from the viewpoint of achieving high specificity for hydrogenolysis of the alpha-hydroxyl group. In this case, the amount of formic acid is preferably in excess or great excess (e.g. over 20 times the amount required). In one embodiment, formic acid is used as the solvent for the reaction either alone or in combination with another solvent.

The reaction proceeds smoothly at elevated temperatures, preferably at the reflux temperature. After the reaction, the catalyst is removed, typically by filtering, the solvent is removed by evaporation and the solid product is then isolated by conventional means such as crystallization from water. If desired the compound of formula (3) can be isolated as a salt of a base or acid instead of as the free base.

The hydrogenolysis techniques of our invention as described above are advantageous in that the introduction of halides and halogenated substances into the reaction mixture is avoided as are the corresponding potential impurities and/or side reactions associated therewith. For example, the use of phosphorous tetraiodide with the alpha hydroxylester as taught in Schmitt et al. appears to provide the ester product in a purity of about 90%. About 6% is side product and about 3% is unreacted starting material. The hydrogenolysis techniques of the present invention have been found, unexpectedly, to provide excellent selective removal of the alpha-hydroxyl group and to provide the compounds of formula (3) in high purity. For example, the acid compound of formula (3), when isolated, typically has a purity of at least 95%, preferably at least 97%, and more preferably at least 98%, without the need to perform a special purification step. Such high purity is advantageous for commercial scale production.

From the acid compound of formula (3), the compounds of formula (1) can be readily made by methods of amidation that are well known in the art. For example, the acid of formula (3) can be reacted with an amidation agent either directly or after activation of the intermediate into an acylchloride, an anhydride, an activated ester, or an activated amide. The amidation reagent includes an amine of the formula $HNR^1R^2$ and ammonia. Typically, an amine is used as the amidation reagent in the presence of carbonyldiimidazole. The process parameters for this reaction are well known in the art (see U.S. Pat. No. 4,382,938 discussed above). Another technique uses an amine amidation agent in the presence of oxalylchloride/dimethylfonmamide. A preferred amidation agent is dimethylamine.

The produced compounds of formula (1) are generally solids and they can be isolated by conventional methods including filtration and precipitation after adding a proper diluent. Advantageously, the excess amine, if any, is removed from the reaction mixture before isolation of the compound of formula (1) is attempted. The compounds of formula (1), when isolated or recovered by conventional means are generally at least 98% pure and usually more than 99% pure, without the need to carry out subsequent purification or the use of special purification/isolation techniques such as HPLC. For clarity, although filtering and crystallization are both technically purification techniques, the "purification" or "special purification" step that is generally unnecessary in the context of the present invention refers to performing a purification technique after the first recovery or isolation of the compound. Such a duplicative step is not needed in order to attain the above-mentioned purity levels of at least 98% for compounds of formula (1) and at least 95% for compounds of formula (3). The high purity level of the compounds of formula (1) is especially advantageous in that it is attained with the free base as opposed to the salt. Moreover, it is attainable reliably, even on an industrial scale.

Another advantage of the preferred embodiments of the present invention is that the free base has a low content of a halogen or halogen-containing compound. Unlike several of the prior art processes, the present invention is not required to use a halogen in the reduction of the alpha-hydroxyl group. Accordingly, no chloride ions or iodide ions are likely to be present in the reaction medium and thus unlikely to become impurities in the solid form of the compound of formula (1). In this context, the composition preferably contains not more than 1% total impurities and not more than 0.1% of a halide ion or a compound thereof. The impurity percentages used herein are based on weight percent.

The compounds of formula (1) can be converted into their corresponding salts of inorganic or organic acids, preferably pharmaceutically acceptable acids, by methods well known in the art. Examples of suitable acid addition salts include hydrochloride, hydrobromide, sulfate, maleate, fumarate, tartrate, mesylate, and tosylate. Additionally, it should be understood that the compounds of formula (1) and their salts include hydrate, solvate and anhydrous forms unless otherwise specified.

The above-mentioned high purity of the free base not only provides for a highly pure salt form, but also facilitates crystal formation. Specifically, it has been discovered that the compounds of formula (1) have difficulty forming crystalline salts; sometimes with poor yields and in a non-crystalline state. Apparently, this difficulty lies in the impurity level of the free base. The highly pure free base of the present invention allows for good yields in the preparation of crystalline salt forms and usually without the need to purify.

Although each step of the synthesis provides good purity, it is permitted to carry out a subsequent purification step on any of the intermediates such as with activated charcoal, silica gel, kieselguhr, etc. Crystallization from a proper solvent is another form of purification. However, such is normally not necessary and is typically only employed for characterization purposes.

The compounds of formula (1), and in particular the substantially pure forms discussed above, are useful in pharmaceutical applications. The compounds of formula (1) and more preferably a pharmaceutically acceptable acid addition salt thereof, can be administered to a patient as a hypnotic, anxiolytic or anticonvulsive agent. Such utility is already known in the art. The compounds of formula (1) or their salts can be combined in an effective amount with pharmaceutically acceptable carriers or diluents to form a pharmaceutical composition. An effective amount to cause a hypnotic, anxiolytic or anticonvulsive effect is well known in the art and/or may be determined from common knowledge and practice using only routine skill. The pharmaceutical composition may be an oral dosage form or a parenteral dosage form and may contain other ingredients in addition to a carrier and/or diluents. Preferably the composition is an oral dosage form such as a tablet or capsule.

EXAMPLES

The invention will now be further described by the following non-limiting examples.

Example 1

2-(p-tolyl)-6-methylimidazo[1,2a]pyridine-3-(2'-hydroxy)acetic acid (Compound (5), Y=Z=methyl)

Suspend 22 g of 2-(p-tolyl)-6-methylimidazo[1,2a]pyridine in 100 ml of dichloroethane, add 10 g of glyoxylic acid monohydrate and heat to reflux for 1.5 hours. Allow to cool to room temperature, filter off the solid and wash it by 2×100 ml of dichloromethane. Dry the product in vacuum oven at 40° C.

Yield: 28 g of the title compound, m.p. 162–164C (degr.), purity 97.9%(HPLC), NMR (400 MHz, DMSO-d6, TMS standard, 303K, delta scale): 8.35 (bs, 1H, 5-H) 7.72 (d, 2H, phenyl-H), 7.55 (d, 1H, 8-H), 7.30 (d, 2H, phenyl-H), 7.19 (dd, 1H, 7-H), 5.67 (s, 1H, 1'-H), 2.37 (s, 3H, phenyl-CH3), 2.31 (s, 3H, 6-CH3).

Example 2

2-(p-tolyl)-6-methylimidazo[1,2a]pyridine-3-acetic acid (Compound (3), Y=Z=methyl)

Dissolve 50 g of the alpha-hydroxy acid from the Example 1 in 500 ml of formic acid, add 5 g of 10% palladium/carbon catalyst and heat the mixture for 20 hours under stirring to reflux. Cool the mixture to room temperature, remove the catalyst by filtration and evaporate the filtrate under reduced pressure. Add 1000 ml of water to the evaporation rest under stirring while a solid precipitate is obtained. Separate the solid by filtration, wash it with 2×300 ml of cold water and dry the product in vacuum oven at max. 40° C.

The yield is 38 g of the title compound, m.p. 142–145 C (dec.), purity 99% (HPLC) NMR (400 MHz, DMSO-d6, standard TMS, delta scale): 8.64 (bs, 1H, 5-H), 7.98 (d, 1H, 8-H), 7.76 (d, 1H, 7-H), 7.61+7.42 (d+d, 4H, phenyl-H) 4.20 (s,2H, CH2), 2.45+2.41 (s+s, 6H, methyl-H).

Example 3

2-(p-tolyl)-6-methylimidazo[1,2a]pyridine-3-acetic acid (Compound (3), Y=Z=methyl)

Dissolve 15 g (0.067 mol) of 2-(p-tolyl)-6-methylimidazo[1,2a]pyridine in 100 ml of formic acid and add under stirring 6.2 g (0.067 mol) of glyoxylic acid monohydrate and reflux the resulting mixture for 1.5 hours. Add 0.75 g of 5% Rh/C catalyst and reflux the mixture for 9 hours while 50 ml of formic acid/water mixture is distilled off. Filter the reaction mixture after cooling through Hyflo (TM) and evaporate the filtrate under reduced pressure at 40° C. Add 70 ml of water to the reaction mixture under stirring. Filter the solid precipitate and wash with 2×15 ml of cold water. Dry in vacuum oven at 50° C.

The yield is 15.5 g of the title substance, purity 99% (HPLC) (same identification data as in example 2).

Example 4

N,N-dimethyl-2-(p-tolyl)-6-methylimidazo[1,2a]pyridine-3-acetamide (Zolpidem, Compound (1), $R^1=R^2=Y=Z$=methyl)

Suspend 10 g of the product from the Example 2 in 500 ml of tetrahydrofuran and add 8.7 g of carbonyldiimidazole. Heat the mixture for 2 hours under reflux and then cool to 35° C. Add 25 ml of 2N solution of dimethylamine in tetrahydrofuran, stir at the same temperature for 1 hour, add next 25 ml of the same dimethylamine solution and stir for next 30 minutes. Evaporate the solvent under reduced pressure, dissolve the same temperature for 1 hour, add next 25 ml of the same dimethylamine solution and stir for next 30 minutes. Evaporate the solvent under reduced pressure, dissolve the evaporation rest in 500 ml of ether and allow to stand overnight. A white solid is formed. Add 100 ml of n-hexane to the mixture, filter the solid off and wash with 50 ml of hexane. Dry the solid in a vacuum oven at 40° C.

The yield is 7.0 g of the title product, m.p. 193 C. Purity 99.5% (HPLC).

Example 5

N,N-dimethyl-2-(p-tolyl)-6-methylimidazo[1,2a]pyridine-3-acetamide (zolpidem, compound (1), $R^1=R2=Y=Z$=methyl)

Suspend 5 g of 2-(p-tolyl)-6-methylimidazo[1,2a]pyridine-3-acetic acid in 50 ml of dry dichloromethane and add 2.5 g of oxalylchloride under stirring at room temperature. Then, add slowly under stirring 5 drops of dimethylformamide (gas formation occurs) and, after 3 hours, add 1.1 g of oxalylchloride. Stir the reaction mixture for 1 hour then bubble slowly gaseous dimethylamine through the reaction mixture for 1.5 hours. After termination, wash the reaction mixture with 2×10 ml of water, dry the organic phase with sodium sulfate and evaporate the solvent under reduced pressure. After adding 25 ml of ethyl acetate to the rest, a solid precipitates. Filter off the precipitate, wash with 2×5 ml of ethyl acetate and dry in a vacuum oven at 40° C.

The yield is 4.3 g of the title compound, identity confirmed by NMR, purity 99.1% (HPLC).

A second crop of the product (0.3g) can be obtained from the filtrate after evaporation and treating with 2 ml of ethyl acetate.

Example 6

Zolpidem Hemitartrate

Dissolve 1 g of zolpidem in 10 ml of methanol and add a solution of 0.244 g of L-tartaric acid in 5 ml of methanol. After cooling, white crystals are formed. Collect the solid by filtration, wash with cold methanol and dry.

The U.S. Patents mentioned above are each hereby incorporated by reference herein in their entirety.

The invention having been described, it will be readily apparent to those skilled in the art that further changes and modifications in actual implementation of the concepts described herein can easily be made or may be learned by practice of the invention, without departing from the spirit and scope of the invention as defined by the following claims.

We claim:

1. A process, which comprises reacting a compound of formula (2):

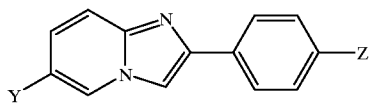

(2)

wherein Y and Z each independently represent a lower alkyl group; with glyoxylic acid or a compound of formula (6):

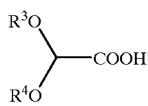

(6)

wherein $R^3$ and $R^4$ each independently represent hydrogen or a lower alkyl;
to form a compound of formula (5):

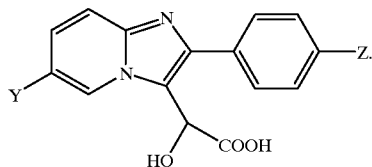

(5)

2. The process according to claim 1, wherein Z is methyl.
3. The process according to claim 2, wherein Y is methyl.
4. The process according to claim 1, wherein $R^3$ and $R^4$ are both hydrogen.
5. The process according to claim 1, wherein $R^3$ and $R^4$ are both a lower alkyl.
6. The process according to claim 5, wherein $R^3$ and $R^4$ are both ethyl.
7. The process according to claim 1, which further comprises removing the alpha hydroxyl group of the compound of formula (5) with a hydrogenolysis agent in the presence of a hydrogenolysis catalyst to thereby form a compound of formula (3):

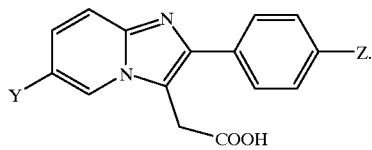

(3)

8. The process according to claim 7, wherein Z is methyl.
9. The process according to claim 8, wherein Y is methyl.
10. The process according to claim 7, wherein said hydrogenolysis agent is selected from the group consisting of formic acid, phosphonic acid, phosphinic acid, alkali metal salts of said acids, and hydrogen gas.

11. The process according to claim 10, wherein said hydrogenolysis catalyst is selected from the group consisting of palladium, platinum, and rhodium.

12. The process according to claim 7, wherein said hydrogenolysis source is formic acid and said hydrogenolysis catalyst is palladium supported on carbon.

13. The process according to claim 12, wherein said formic acid is also the solvent for said reaction.

14. The process according to claim 7, which further comprises converting said compound of formula (3) to a compound of formula (1) by reaction with an amidation agent:

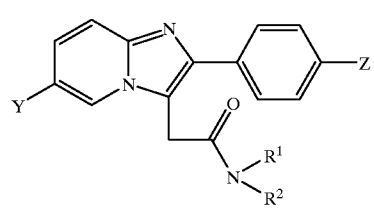

(1)

wherein $R^1$ and $R^2$ each independently represent hydrogen or a lower alkyl group.

15. The process according to claim 14, wherein said amidation agent is an amine of the formula $HNR^1R^2$.

16. The process according to claim 15, wherein said conversion is carried out in the presence of carbonyldiimidazole.

17. The process according to claim 14, wherein $R^1, R^2, Y,$ and Z are each methyl.

18. The process according to claim 17, which further comprises forming a pharmaceutically acceptable acid addition salt of said compound of formula (1).

19. The process according to claim 18, which further comprises combining a pharmaceutically effective amount of said pharmaceutically acceptable acid addition salt with a pharmaceutically acceptable carrier or diluent to form a pharmaceutical composition.

20. The process according to claim 19, wherein said pharmaceutical composition is an oral dosage form.

21. The process according to claim 17, which further comprises recovering said compound of formula (1) as a solid in a purity of not less than 98%.

22. The process according to claim 21, wherein said purity is at least 99%.

23. A process which comprises: (a) reacting a compound of formula (2):

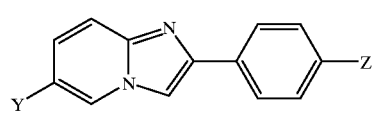

(2)

wherein Y and Z each independently represent a lower alkyl group; with a compound of formula (6):

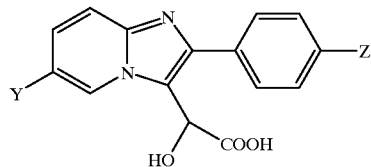

wherein $R^3$ and $R^4$ each independently represent hydrogen or a lower alkyl;

to form a compound of formula (5):

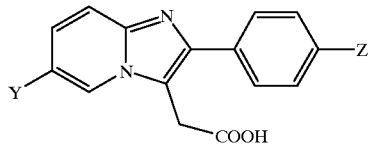

(b) removing the alpha hydroxyl group of said compound of formula (5) with excess formic acid in the presence of palladium or rhodium supported on carbon to thereby form a compound of formula (3):

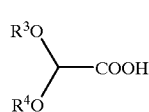

and (c) converting said compound of formula (3) to a compound of formula (1) by reaction with an amidation agent:

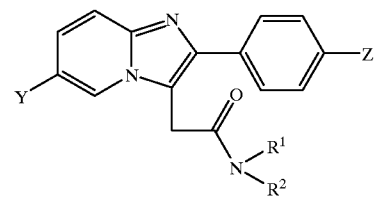

wherein $R^1$ and $R^2$ each independently represent hydrogen or a lower alkyl group.

24. The process according to claim 23, wherein said compound of formula (5) is not isolated before carrying out said step (b).

25. The process according to claim 24, wherein said steps (a) and (b) are carried out in formic acid as the solvent.

26. The process according to claim 23, wherein Y, Z, $R^1$, and $R^2$ are each methyl.

27. The process according to claim 23 which further comprises (d) recovering said compound of formula (1) as a solid, said compound having a purity of at least 99%.

28. The process according to claim 23 which further comprises forming a pharmaceutically acceptable acid addition salt of said compound of formula (1).

29. A compound of formula (5):

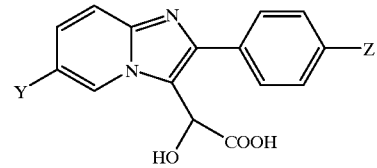

wherein Y and Z each independently represent a lower alkyl group.

30. The compound according to claim 29, wherein Y and Z are both methyl.

* * * * *